United States Patent [19]

Mulzet

[11] 4,447,221

[45] May 8, 1984

[54] CONTINUOUS FLOW CENTRIFUGE ASSEMBLY

[75] Inventor: Alfred P. Mulzet, Princeton Jct., N.J.

[73] Assignee: International Business Machines Corporation, Armonk, N.Y.

[21] Appl. No.: 388,770

[22] Filed: Jun. 15, 1982

[51] Int. Cl.³ .............................................. B04B 7/08
[52] U.S. Cl. .................................................... 494/45
[58] Field of Search ................... 494/6, 10, 45, 21, 41, 494/43; 209/155, 208

[56] References Cited

U.S. PATENT DOCUMENTS

| 4,094,461 | 6/1978 | Kellogg | 494/43 |
| 4,278,202 | 7/1981 | Westberg | 494/45 |
| 4,283,276 | 8/1981 | Grant | 494/41 |

Primary Examiner—Robert W. Jenkins
Attorney, Agent, or Firm—Sughrue, Mion, Zinn, Macpeak, and Seas

[57] ABSTRACT

A continuous flow centrifuge system having a disposable fluid container of constant cross-section mounted in a circular channel. The channel, defining a separation region, has a constant height and side walls of diverging spirals to increase the cross-sectional area from inlet to outlet. The container expands dynamically to conform to the claimed geometry and the collection chamber is attached to the container to obtain the separated fluid fractions. The channel may be in an insert, defined between the walls of the insert and the rotor bowl or in a rotor head assembly.

18 Claims, 6 Drawing Figures

CONTINUOUS FLOW CENTRIFUGE ASSEMBLY

This application is related to application Ser. No. 803,007, filed on June 3, 1977, by R. M. Kellogg et al entitled "Centrifuge Assembly" and assigned to the assignee of this application.

BACKGROUND OF THE INVENTION

This invention is related to continuous flow centrifugal separation of blood, and in particular, to an improved centrifuge assembly utilizing a disposable blood container. The prior art is replete with a number of concepts for separating the components of blood utilizing complex channeling or grooves in the centrifuge bowl together with fluid connections for input/output functions. Such devices are not only expensive to manufacture but difficult to clean and sterilize for each use. Such continuous flow systems are shown in U.S. Pat. Nos. 3,489,145; 3,519,201; and 3,655,123.

Given these cost and operational problems, systems have evolved using bag structures which do not require a channel directly receiving the fluid to be separated. Such systems are shown in U.S. Pat. Nos. 3,748,101 and 4,007,871.

U.S. Pat. No. 4,278,202 relates to a centrifugal system having a flow path that increases in cross-sectional area from inlet to outlet. The increase in area occurs by diverging spirals of the side walls as well as increasing the depth of the channel. The separation container is made to correspond to this channel configuration and employs an internal fluid connection for the input running along the inner circumferential length of the container. The entire channel is inclined to the rotor axis at an acute angle. Such a device is difficult to manufacture given the geometry and the container is expensive to make on a mass production basis. Also, the geometry of the system makes it difficult to collect fractions in the buffy coat given the lack of a stable collection chamber. The patent perceives only collection of the most dense and the least dense fractions with the output portions as shown.

Reference is made to U.S. Pat. No. 4,094,461 which discloses a disposable centrifuge bag placed between the inner wall of the centrifuge bowl and a filler or centerpiece. The '461 patent represents a significant advance in the prior art by defining not only a disposable centrifuge bag but also a collection region which acts in a self-regulating manner. While the subject matter of the '461 patent has found widespread practical application, there still remain a number of areas for improvement.

First, a standing requirement in extra-ventricular systems of the type defined by the prior art is to reduce the volume of blood which is processed outside of the body. Reducing the blood volume requirements of the separation system allows the procedure to be tolerable for a wider range of donors. For example, physically smaller donors having a less than "normal" blood volume themselves cannot tolerate a procedure that requires their limited blood volume to be extra corporeal. Also, a reduction insures that during such procedures, donors will not be unduly deprived of cells that have not been collected. Those sick donors having specific needs for certain types of cells, such as a chronic anemic requiring red cells, cannot accept short term losses. Hence, it is desirable to define a system having minimum extravascular volume requirements that still retains separation and collection efficiently at existing levels.

A second requirement in such continuous flow blood centrifuge systems is to define a device capable of automatic priming (filling) and complete emptying of the container. At the beginning of each run prior to establishing the blood flow, air must be first expelled from the container and the device primed with a sterile solution as saline. Current systems require operator control for this initial step such that procedures are operator intensive in a field where skill levels among individuals are difficult to maintain at acceptable standards. At the end of each procedure, the container must be emptied of all red cells which remain. This is conventionally done also by operator control using the introduction of saline into the chamber which itself displaces packed red cells from the chamber into the collection zone where they can be returned to the donor.

It is implicit that such systems must be maintained sterile and capable of easy cleaning to achieve sterility in the blood handling equipment. Moreover, separation of the blood fractions must be conducted in a manner that does not injure or destroy blood cells. Cell fragility is an important facet in evaluating the overall efficacy of any system.

Accordingly, while the prior art evidences significant advances in continuous flow blood centrifugation systems, areas of safety, efficiency, and automation remain for continued development. Given the stringent safety requirements implicit in any in vivo blood handling system, improvements in collection efficiency and operation must be made without compromising the overall efficacy of the procedure. Accordingly, techniques which may attempt to achieve higher levels of efficiency are fundamentally untenable if they have a propensity for reducing any paramount safety criteria of such systems, such as criteria of sterility and blood fragility.

SUMMARY OF THE INVENTION

Given the deficiencies of the prior art, it is an object of this invention to provide for an improved separation chamber for use with a continuous flow blood centrifuge.

Another object of this invention is to provide an improved rotor assembly utilizing a disposable container for separating blood into different fractions thereof while reducing the overall volume requirements of such a system.

A further object of this invention is to provide an improved rotor assembly which is self priming and self emptying under computer control thereby eliminating the need for operator supervision.

Yet another object of this invention is to provide an improved rotor assembly and its associated blood container for centrifuging blood which is simple and economic in construction yet utilizing disposable components and interchangeable inserts.

An additional object of this invention is to define a system where the outer wall pumps red cells down the channel, even in conditions of no flow, to eliminate any stagnant portions in the channel.

The foregoing and other objects, features and advantages of this invention will be apparent from the following detailed description of the preferred embodiments of this invention as illustrated in the accompanying drawing and described in connection with the description of the preferred embodiments as follows.

Briefly, in accordance with the present invention, the separation system uses a disposable, semi-rigid container. This container is placed in a channel having an outer wall spiraling gradually outward from the blood inlet port of the container and an inner wall which spirals inwardly. Accordingly, from the input port, the cross-section of narrowest area, the cross-section of the channel continuously increases in width having its widest section at the end of the separation-channel which forms an input to a collection region. This increase in cross-section occurs without a change in depth; that is, the height of the channel remains uniform.

The channel geometry can be defined in several different implementations. First, it can be defined in the context of an insert placed in the rotor bowl with, the blood container placed in that insert. Secondly, the channel can be defined by the outer wall of an insert and the inner wall of the rotor bowl. The container is placed between the insert and rotor bowl wall. Thirdly, the channel geometry can be defined solely within a removable rotor head. The container is placed in the rotor head.

Blood to be fractionated is supplied to the inlet end of the circular blood container. Under the influence of centrifugal force, the container expands to correspond to the wall geometry of the channel and the blood is separated into regions comprising its various fractions, the heavier red cells moving radially outward while the lighter plasma remaining at the radially inwardmost position. The white cells and platelets sediment to the interface between the plasma and red cells to define the buffy layer. In a collection region output tubes are disposed at different radial distances constituting those separation zones to collect the blood fractions. Hence, in one embodiment the collection container assumes a dynamic shape, that of the channel, different from its static constant cross-sectional shape. In a second embodiment, the static and dynamic shapes are identical and match the channel cross-section.

Given the channel geometry, an overall reduction in the extra vascular blood volume results thereby making any separation and collection procedure more tolerable for a wide range of donors. Preferably the input cross-section is 0.25 the size of a conventional channel. Secondly, the channel geometry allows the device to be both self priming and self emptying. The procedure is therefore less operator intensive than conventional techniques.

The semi-rigid blood container may be made of suitable plastic material, such as medical grade polyvinyl chloride (PVC). The wall thickness is selected to provide necessary rigidity for handling yet allow expansion, if necessary in the case of one embodiment during use.

BRIEF DESCRIPTION OF THE DRAWINGS

In the drawings, reference characters refer to identical parts in each of the different views.

DESCRIPTION OF THE PREFERRED EMBODIMENTS

Figure 1:
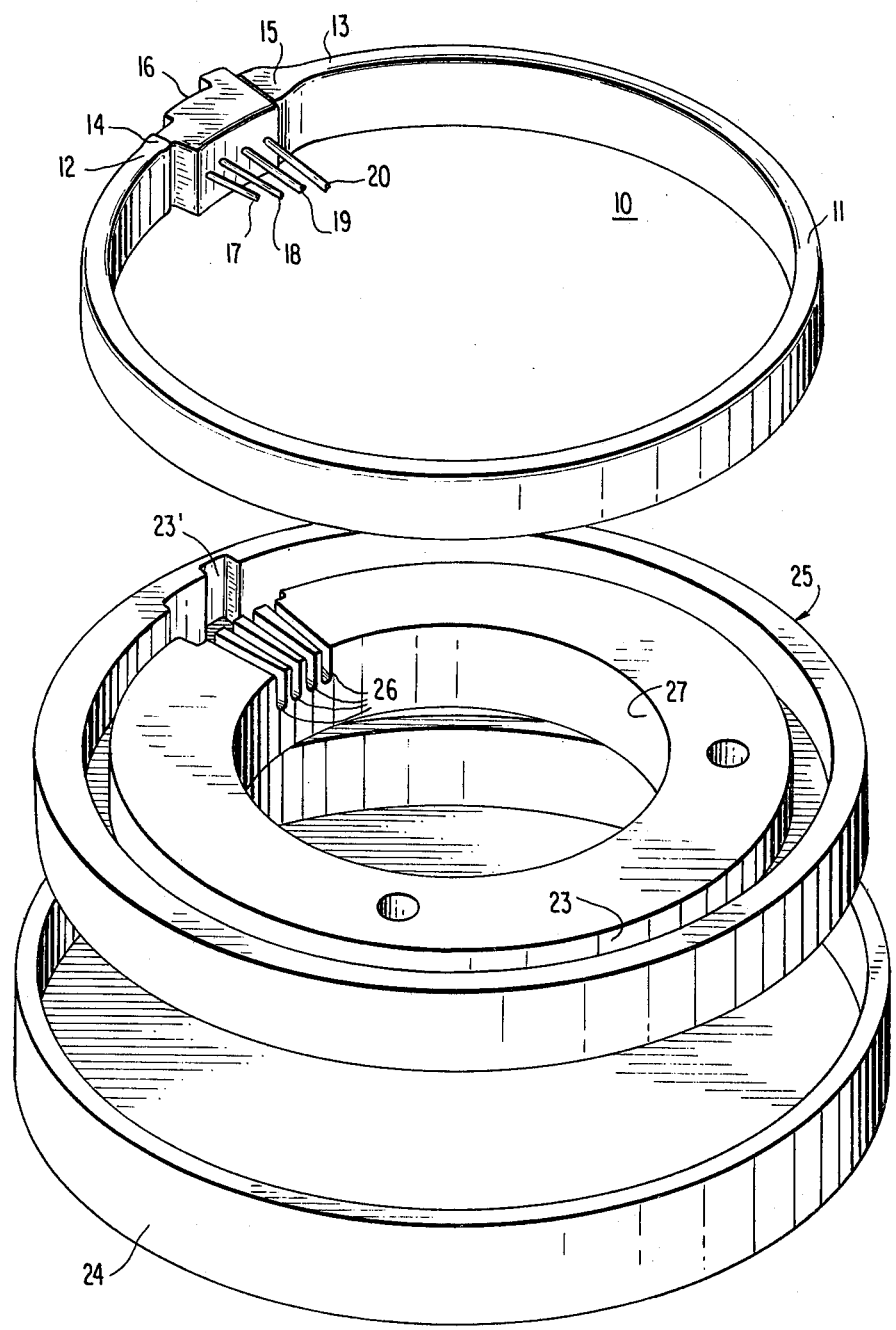
FIG. 1 is a diagrammatic perspective view showing a centrifuge bowl, a filler or center piece, and a fluid container in an exploded relation in accordance with a first preferred embodiment of the invention.

Referring now to FIG. 1, a blood container 10 comprises a length of semi-rigid plastic tubing 11, preferably made of medical grade polyvinyl chloride and having a substantially rectangular cross-section. That is, tubing 11 in a static condition is of uniform cross-section. The container 10 comprises two components, a separation channel 11 formed from the tubing and a collection chamber 16 for extracting those blood components that have been separated in the separation channel. Although FIG. 1 illustrates a collection chamber 16, it is apparent that such a distinct element is not required. Output connections can be made directly to the channel 11.

The tubing 11 and collection chamber 16 maybe formed in a circle as shown in FIG. 1 having ends 12 ands 13 joined to corresponding ends 14 and 15 of the collection chamber 16. Joining can be done by cementing or heat sealing those end portions. The blood container 10 may alternately be an elongate body, not joined at its ends.

Because, as will be described herein, the separation channel 11 expands under dynamic conditions, the output end 13 has a flared portion of cross-sectional area substantially identical to that which the channel assumes while spun. Hence, the cross-sectional area of the outlet end 13 is greater than that at the input end 12. Correspondingly, the matching end portions of the collection chamber 16 have different cross-sectional areas. The output end 14 of the collection chamber has a cross-sectional area less than the input end 15. The collection chamber itself while shown schematically may be of the type disclosed in U.S. Pat. No. 4,094,461. Other configurations for the collection chamber may also be employed.

Access tubes 17, 18, 19, and 20 couple the collection chamber 16 to an Input/Output portion of the system not shown. For example, a rotating seal of the type disclosed in U.S. Pat. No. 3,489,145 may be utilized. Alternatively, other I/O arrangements may be employed including types that do not employ seals. Connection 17 serves as an input connection while the remaining connections 18–20 define output porting for the separated blood components collected in the collection chamber 16. The terminal ends of these tubes extend to different radial positions in the collection chamber.

The fluid container 10 is adapted for placement in a centrifuge to effectuate fractionalization of input fluid such as whole blood. FIG. 1 shows a first preferred embodiment of the centrifuge arrangement utilizing a centrifuge bowl 24 and a rigid insert or filler 25. The filler 25 is inserted into the centrifuge bowl and may have, as shown, a series of holes used for convenience of lifting the filler and also to serve as balancing holes for the complete assembly. As shown in FIG. 1 and discussed in greater detail vis-a-vis FIG. 3, a circular groove 23 of expanding cross-sectional area is placed in the filler 25 into which the blood container 11 is inserted.

Radial grooves 26 are also placed in the insert for accommodating tubes required for the I/O connection in the system. The groove 23 also has a portion 23' to accommodate the collection chamber.

The centrifuge bowl 24 may be formed of any suitable materials such as metal or plastic or a combination thereof. The filler or center piece 25 may also be formed of a suitable material such as plastic formed by molding or machining. As is well known in this technology, the filler 25 is retained in place on a central hub or a plurality of distributed bosses or pins, not shown. The filler piece 25 has a central opening 27 which accommodates the I/O connections. For example, if a rotating seal assembly is utilized, tubing 17-20 will terminate in the central portion 27 where the seal will be disposed.

Figure 2:
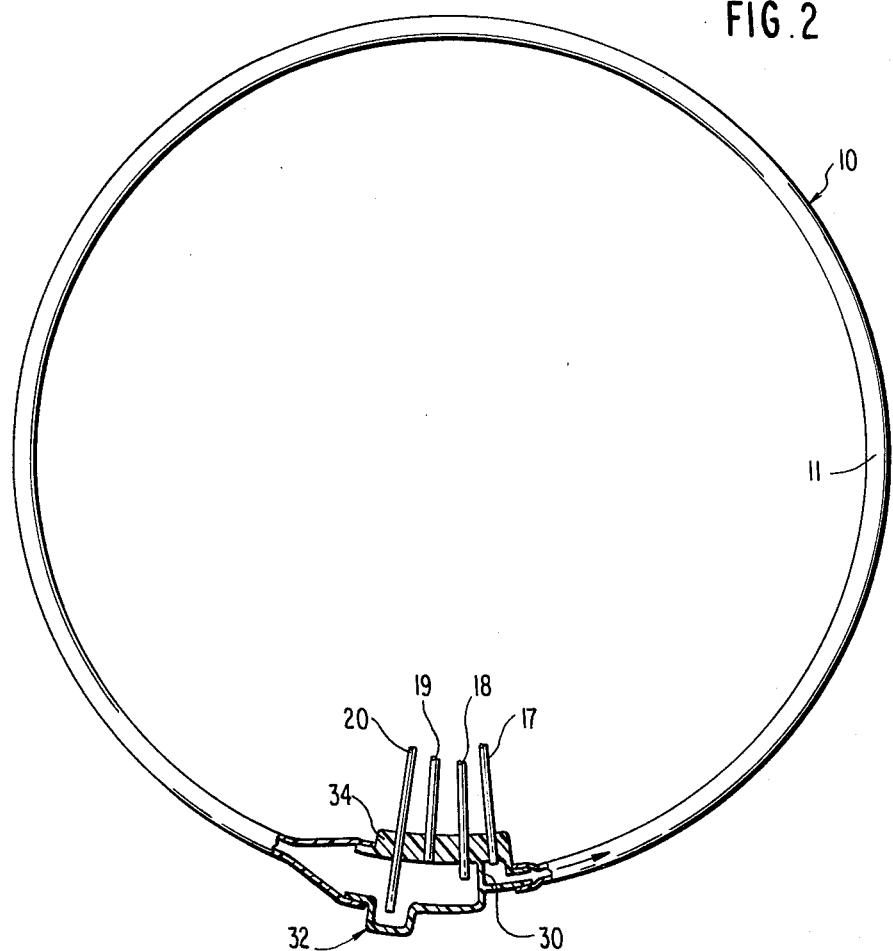
FIG. 2 is a diagrammatic plane view of the blood container showing the radial location of inlet and outlet ports.

Referring now to FIG. 2, the blood container 10 is shown comprising an extruded tube 11 made from a semi-rigid PVC material of substantially rectangular cross-section. The tube 11 is formed into a circle having a barrier 30 to separate the inlet portion of the tube 11 forming the separation zone from the comlection chamber. Blood inlet line 27 is disposed on one side of the barrier 30 while outlet ports 18-20 are placed on the opposite side. Blood to be separated enters the tube via inlet line 17 and flows in the direction of the arrow of FIG. 2. As a result of centrifugation of the input fluid, separation occurs in the extruded tube 2 such that distinct fractions of the blood are delineated. The fraction of greatest density, red blood cells are formed at the outside, the fraction of the next greatest density, the buffy layer containing white blood cells and platelets forms in a narrow center band while, the innermost and least dense layer is plasma. Accordingly, three outlets ports are positioned at different radial distances to collect these fractions. The red blood cell outlet port 20 is positioned at the greatest radial distance while, the plasma port 19 is positioned most inward. At an intermediate location, the white blood cell outlet port 18 is positioned in the collection region. Alternatively, the collection zone using a dam arrangement as described in U.S. Pat. No. 4,094,461, can also be employed.

A molded connector 32 is used to connect the ends of the extruded tube 11 into a complete circle. The channel 23 has a portion 23' to receive the molded connector. Likewise, a support member 34 for the tubing 17-20 will fittingly engage into the recess 23'. The support 34 is used to accurately fix and hold the tubing 17-20 in the collection region.

Alternatively, the connector 32 may be deleted and the tubing 17-20 merely inserted through the inner wall of tube 11. The tubing can be secured at the appropriate radial locations for collection by appropriate techniques of affixation where they pass through the inner wall.

Figure 3:
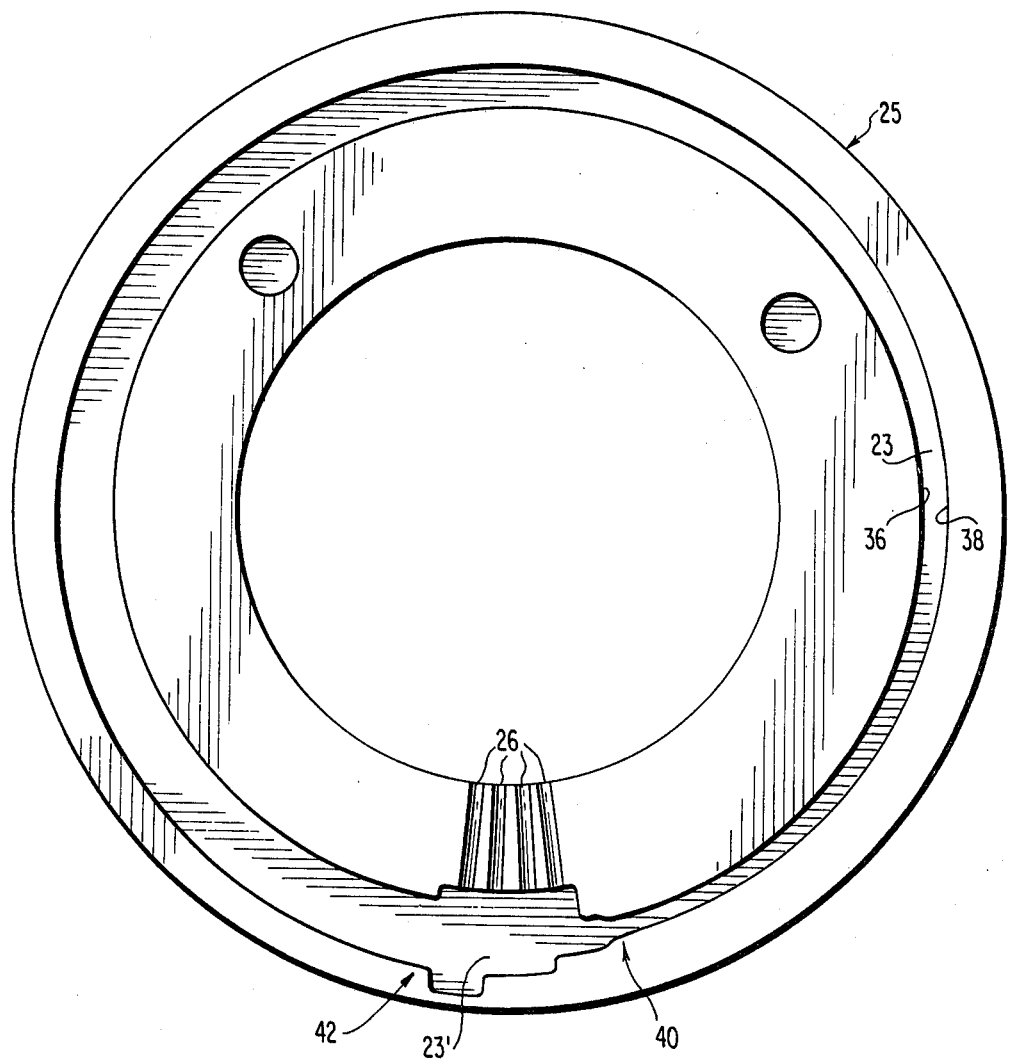
FIG. 3 is a plane view of a filler or center piece showing the spiral geometry of the separation channel in accordance with this invention.

Referring now to FIGS. 1 and 3, details of the separation channel are shown. As shown in FIG. 3, the insert 25 has a slot 23 formed by inner wall 36 and outer wall 38. From the input portion of the channel 40, the inner wall 36 spirals gradually inward while the outer wall 38 spirals gradually outward. This spiraling of the inner and outer walls causes the cross-sectional area of the channel 23 to progressively increase from the intake portion 40 to the collect region 42. As shown in FIG. 1, the overall height of the channel remains constant, that is, a uniform depth of the channel is defined in the insert 25. Accordingly, the increase in cross-sectional area occurs without a change in depth.

It is understood that FIG. 3 exaggerates the spiraling for purposes of illustration. The inclination angle of each spiral is small, generally less than 1°. Preferably, the inclination is in the order of 0.25°.

The blood container 10 has in its static condition a cross-sectional area closely matching the cross-sectional area at the input point 40. This input cross-sectional area is materially less than that utilized in any prior art devices such as those disclosed in U.S. Pat. No. 4,094,461 or U.S. Pat. No. 4,278,202. It is about 0.25 the area at the end of the separation channel. At the output point, that is, in zone 42 forming an inlet to the collection region, the cross-sectional area is substantially the same as that in, for example, the prior art '461 blood container.

An alternative container configuration can be achieved by blow molding or the like to have a configuration than is constant in both static and dynamic conditions to match channel geometry. It is therefore within the scope of this invention to have a cross-sectional shape to the container that does not change when in use.

In operation, the container 11 is placed in the insert 25 with the tubes 17-20 placed in slots 26. In this static condition, the end 12 of the container 10 will closely conform to the cross-sectional area at the zone 40 of the channel 23. Similarly, the collection region 16 will conform to the cutout portion 23'. However, in the FIG. 2 embodiment the cross-sectional area of the container 10 formed by the extruded tube 11 throughout the remaining portion of the separation channel will have in a static condition, that is, when initially inserted into the insert 25, a cross-sectional area less than that of the channel 23. This subcombination of container and insert is then placed in the rotor bowl 24 and appropriate fluid couplings establishing fluid continuity to and from the donor are established.

The centrifuge assembly is then spun up at low RPM and the inlet port 17 initially establishes fluid communication between the container 10 and a priming fluid to purge any air. Air is forced along the inside spiral and removed via the plasma port. The output to the donor is shunted until priming is complete and then the centrifuge RPM is increased to blood separation speeds. The donor's blood is inputted into the system for separation. The combination of fluid pressure and centrifugal force urges the walls of the tube 11 to conform to the wall geometry of the inner and outer walls 36 and 38. Accordingly, the cross-sectional area of the tube 11 changes from its static constant cross-sectional area to one of increasing cross-sectional area in its dynamic condition. The outlet ports 18-20 collect the targeted blood fractions and to return to the donor those fractions not required for collection. Hence, a closed loop continuous flow separation process is defined wherein blood from the donor is supplied to the system via inlet tube 17, is separated in tube 11 having a geometry corresponding to channel 23, separated in collection region 16 with the targeted separated fraction accumulated in a container, not shown, and the remaining fractions returned to the donor.

At the end of a procedure, the container is emptied of any remaining cells, especially packed red cells by purging with saline. The red cells are returned to the donor. The other output ports gate the saline out of the system.

The system shown in FIGS. 1-3 offers important advantages over the prior art. First, the overall volume of extra corporeal blood processed in the separation system is materially reduced since the cross-sectional area of the channel at the input portion is approximately one-fourth that of the output. The output geometry is substantially the same as in the prior art. The reduction in volume in a continuous flow process is important since it makes the procedure tolerable for a wider range of donors. Such a reduction in volume also minimizes any possibility of cell deprivation to the donor during a procedure.

Secondly, important operating advantages occur utilizing the spiral geometry and constant height of the channel 23 to which the tube 11 conforms when in use. The inward spiral of the wall 26 tends to direct any entrained air out the plasma port 19 during start-up and run conditions. That is, at the start of any procedure, air must be expelled from the container 10. When the centrifuge is turned on, air, being less dense than any fluid introduced into the container, is forced to the inner wall and exits through the plasma port 18. The system therefore is self-priming and does not require operator action. Start-up conditions can therefore be monitored under computer control. Similarly, the outward spiral on wall 38 promotes collection of red cells. Those cells, forming the most dense fraction of blood, separate early along the outer wall of the tube. They tend to collect in the separation zone and therefore the outer spiral promotes migration of early separated red cells from the separation region of the tubing 11 into the collect region 16. This pumping of red cells eliminates any stagnant portions in the channel, even during no flow conditions. Red cell removal is therefore promoted by the outer spiral of wall 38.

Maintaining a vertical orientation in the system, when coupled with the inward and outward spirals, increases overall system stability and promotes automatic operation. The vertical orientation of the separation zone formed by the generally rectangular tubing 11, even in its expanded configuration to conform to the cross-section of channel 23, has been shown to be an optimum separation geometry. The elimination of any angular orientation of the tubing while at the same time increasing its cross-sectional area enhances separation.

For purposes of manufacture, a more orthogonal system is easy to manufacture when compared to one requiring varying wall direction on sides and bottom. The formation of the channel is therefore more easily accomplished. The same is true for the containers since conventional techniques for making a tube of constant cross-section can be employed.

Finally, this improved geometry allows automatic termination of any procedure by facilitating removal of any remaining red cells. At the end of a procedure, it is necessary to empty the separation channel 11 and the collection region 16 of any accumulated red cells to insure that the donor is not deprived of that separated fraction. In accordance with the present invention, this final step can be automatically accomplished by introducing saline into the channel which displaces the red cells forcing them down the outer wall of the container 11 for removal in the red blood cell outlet port 20. This action can be done under computer control with no operator action. At the end of the run, the container 10 with its associated tubing is removed from the insert and disposed. Accepted clean-up procedures are employed and a new container is fitted into the insert for a new run.

Figure 4:
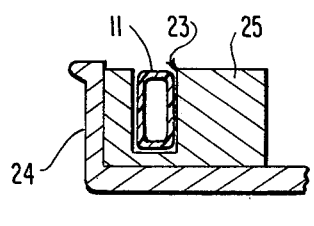
FIGS. 4–6 are cross-sectional elevation views showing three alternative embodiments of forming the channel geometry and placement of the container within that channel.

The first embodiment of this invention perceives the use of an insert 25 having the separation channel 23 formed in that insert. As described, the container fits into the insert. This is shown in cross-section in FIG. 4 where the insert 25 is received in the rotor bowl 24 with the container 11 disposed in the channel 23 formed in the insert.

Figure 5:
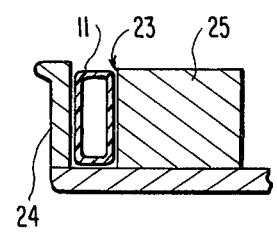

It is apparent, however, that various other techniques may be used to form the channel 23. For example, as shown in FIG. 5, the channel 23 can be formed between the outer wall of the insert 25 and the inner wall of the bowl 24. That is, the outer wall of the insert 25 can be configured to have the inward spiral 36. Correspondingly, the inner wall of the bowl 24 can be formed to define the outer spiraling wall 38. Hence, as shown in FIG. 5, a separation channel can be defined between the bowl 24 and the insert 25 with the container 11 placed between those elements.

Figure 6:
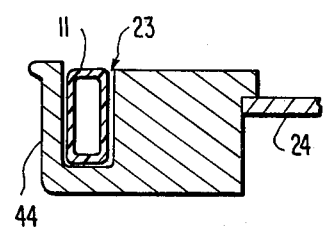

A third alternative is shown in FIG. 6 utilizing a one-piece rotor head assembly 44. In this embodiment, the channel 23 is defined as a groove in the rotor head. No insert is utilized. The rotor head 44 is then joined to the rotor 24 in a manner known in the technology.

Accordingly, the present invention perceives that a plurality of filler pieces 25 may be used to define different channel geometries depending on the procedure which is employed. Such interchangeability allows a common centrifuge system to be used, thereby offering increased versatility. As an alternative to different inserts, different rotor heads may be employed. If, however, such interchangeability is unnecessary, then a one-piece rotor may be used employing the channel geometry as shown in FIG. 2.

From the foregoing description, it is apparent that the present invention provides an improved centrifuge assembly offering unique advantages of efficiency while being economical to fabricate and reducing the requirement of operator control.

The present invention has been particularly shown and described with reference to three preferred embodiments. However, it will be understood by those skilled in the art that other changes may be made herein without departing from the spirit and scope of the invention.

I claim:

1. A centrifuge assembly comprising:
   a rotor,
   means defining a channel in said rotor, said channel having a portion of gradually increasing cross-sectional area formed solely by increasing its radial width, said channel having sidewalls of substantially uniform height and parallel to the axis of rotation of said rotor;
   a disposable hollow container of semirigid material having two ends and received in said channel, said container in a dynamic mode conforming to said channel geometry, and
   fluid connections coupled to said container.

2. The centrifuge assembly of claim 1 wherein said rotor includes a bowl and said means defining a channel is received in said bowl.

3. The centrifuge assembly of claim 1 wherein said container is ring-like and joined at its two ends.

4. The centrifuge assembly of claim 1 wherein said container is an extruded elongate body.

5. The centrifuge assembly of claims 1, 3 or 4 further comprising a fluid collection chamber attached to at least one end of said container.

6. The centrifuge assembly of claims 1, 3 or 4, wherein said container has in a static mode an internal fluid separation path with constant dimensions and expanding in a dynamic mode to conform to said channel geometry and thereby increase the volume of said fluid separation path.

7. The centrifuge assembly of claims 1, 3 or 4 wherein said container has a static shape conforming to it dynamic shape.

8. The centrifuge assembly of claim 1, wherein said means defining a channel in said bowl comprises a rigid insert and said channel is provided in said insert.

9. The centrifuge assembly of claim 1, wherein said means defining a channel in said bowl comprises a rotor head and said channel is provided in said rotor head.

10. The centrifuge assembly of claim 1, wherein said means defining a channel in said bowl comprises a rigid insert and said channel is defined between the inner wall of said rotor bowl and the outer wall of said insert.

11. A centrifuge assembly comprising:
a rotor,
a channel provided in said rotor having a substantially rectangular cross-section that continuously increases in area solely by an increase in width from one end to the other, said rectangular channel having sidewalls of substantially uniform height and parallel to the axis of rotation of said rotor and
a disposable ring-like containing of semirigid material contained in and conforming to said channel, and a collection chamber coupled to said container.

12. The centrifuge assembly of claim 11, wherein a channel is provided in said filler piece received in said bowl.

13. The centrifuge assembly of claim 11, further comprising a rotor head mounted on said rotor and said channel is provided in said rotor head.

14. The centrifuge assembly of claim 11, wherein said rotor is provided with a filler piece and said channel is defined between the inner wall of said rotor and the outer wall of said filler piece.

15. The centrifuge assembly of claim 14, wherein said container includes a partition to separate an input portion of said container from said collection chamber, a fluid inlet port in the inlet portion and output port means in said collection chamber.

16. The centrifuge assembly of claim 14, further comprising a rigid connector joining ends of said container to form a ring-like configuration.

17. Apparatus for separating blood comprising:
a centrifuge having a rotor bowl,
a hollow ring-like disposable container of semirigid material having an inlet end and an output end, said container defining a separation path therein of constant cross-sectional area in a static state,
a collection chamber coupled to said container,
an insert received in said bowl and having a channel portion therein of substantially rectangular cross-section with said portion thereof increasing in cross-sectional area from an inlet end to an output end, an outward spiral of an outer wall of said channel and an inward spiral of an inner wall thereof while maintaining the height of said rectangular cross-section constant, and
said container contained in said channel and in a dynamic state expanding to conform to the cross-sectional area of said channel and enlarged the cross-sectional area of said separation path from said inlet end to said output end.

18. The centrifuge assembly of claims 1, 11 or 17, wherein said container has a flared end portion coupling said container to said collection chamber.

* * * * *